(12) United States Patent
MacDonald et al.

(10) Patent No.: US 7,732,420 B2
(45) Date of Patent: Jun. 8, 2010

(54) COMBINATIONS OF TRANSFECTION LIPIDS EXHIBITING INCREASED TRANSFECTION EFFICIENCIES

(75) Inventors: Robert C. MacDonald, Evanston, IL (US); Li Wang, Evanston, IL (US)

(73) Assignee: Northwestern University, Evanston, IL (US)

( * ) Notice: Subject to any disclaimer, the term of this patent is extended or adjusted under 35 U.S.C. 154(b) by 602 days.

(21) Appl. No.: 10/957,977

(22) Filed: Oct. 4, 2004

(65) Prior Publication Data

US 2005/0142179 A1 Jun. 30, 2005
US 2006/0257464 A9 Nov. 16, 2006

Related U.S. Application Data

(60) Provisional application No. 60/508,544, filed on Oct. 3, 2003.

(51) Int. Cl.
*A01N 43/04* (2006.01)
*A61K 31/70* (2006.01)
*C12N 5/00* (2006.01)
*C12N 5/02* (2006.01)
*G01N 33/92* (2006.01)

(52) U.S. Cl. .................. 514/44 R; 435/325; 436/71
(58) Field of Classification Search .............. None
See application file for complete search history.

(56) References Cited

U.S. PATENT DOCUMENTS 5,660,855 A * 8/1997 Male-Brune ............... 424/450
6,638,767 B2 * 10/2003 Unger et al. ............... 435/458
6,649,780 B1 * 11/2003 Eibl et al. ................... 554/110
6,743,779 B1 * 6/2004 Unger et al. ............. 514/44 R
2001/0031740 A1 * 10/2001 Unger et al. ................ 514/44

OTHER PUBLICATIONS

Tarahovsky, Y., et al. "DNA Release from Lipoplexes by Anionic Lipids: Correlation with Lipid Mesomorphism, Interfacial Curvature, and Membrane Fusion", Biophysical Journal, vol. 87, pp. 1054-1064 (Aug. 2004).
Pedroso de Lima, M., et al. "Cationic lipid-DNA complexes in gene delivery: from biophysics to biological applications", Advanced Drug Delivery Reviews, vol. 47, pp. 277-294 (2001).
Struck, D., et al. "Use of Resonance Energy Transfer To Monitor Membrane Fusion", Biochemistry, vol. 20, pp. 4093-4099 (1981).
MacDonald, R., et al. "Physical and Biological Properties of Cationic Triesters of Phosphatidylcholine", Biophysical Journal, vol. 77, pp. 2612-2629 (Nov. 1999).
Faneca, H., et al. "Association of albumin or protamine to lipoplexes: enhancement of Transfection and resistance to serum", The Journal of Gene Medicine, vol. 6, pp. 681-692 (2004).

* cited by examiner

*Primary Examiner*—Robert M Kelly
(74) *Attorney, Agent, or Firm*—Casimir Jones SC

(57) ABSTRACT

The present invention provides optimized transfection reagents comprising mixtures of cationiclipoids. In particular, the present invention provides DNA delivery vehicles based on identifying the optimal hydrophobicity of novel cationic phospholipid derivatives that, alone or in combination, form complexes with DNA (lipoplexes) and exhibit enhanced transfection activity.

3 Claims, 10 Drawing Sheets

COMBINATIONS OF TRANSFECTION LIPIDS EXHIBITING INCREASED TRANSFECTION EFFICIENCIES

This application claims priority to U.S. Provisional Patent Application Ser. No. 60/508,544, filed Oct. 3, 2003, which is incorporated herein by reference in its entirety.

The present invention was made, in part, under funds from the National Institutes of Health Grant No. GM 52329. The government may have certain rights in the invention.

FIELD OF THE INVENTION

The present invention provides optimized transfection reagents comprising mixtures of cationic lipids. In particular, the present invention provides DNA delivery vehicles based on identifying optimal hydrophobicity of novel cationic phospholipid derivatives that, alone or in combination, form complexes with DNA (lipoplexes) and exhibit enhanced transfection activity.

BACKGROUND

There are approximately four thousand different genetic diseases, many highly debilitating and frequently resulting in death at an early age. Because almost all of these diseases involve a defective protein, conventional treatment is difficult. A direct approach to treating such diseases involves providing a competent gene in the proper cells to compensate for the mutation. This requires some form of effective transfection process. Transfection is a process whereby a nucleic acid, primarily DNA, is transferred to a target cell and codes for an expressed protein. Transfection is implemented typically to modify the gene complement of the recipient cell for controlled expression of a particular gene. The means by which "foreign" DNA can be packaged and delivered to a host cell are many and varied. The most efficient of these make use of viruses, but viral vectors have shortcomings, not the least of which is the potential for immune response or disease transmission. It has become apparent that lipid-like compounds (e.g., lipoids) can be used to deliver DNA to cells. The lipids that are most efficient in delivering DNA to cells are positively charged. Cationic lipids are naturally attracted to and spontaneously form complexes with polyanionic DNA. Such complexes, or "lipoplexes," are useful as transfection vehicles both in vitro and in vivo. Lipoplexes offer several advantages in that they provide a high DNA packing density, lower immunogeneicity, and are likely to be able to transport DNA of considerably larger size than the viral vectors. The possibility of targeting lipidic carriers to specific cell types also makes them attractive candidates for gene therapy. However, the delivery of whole genes is not the only form of gene therapy. Previous research has demonstrated that antisense gene therapy may be useful to inhibit expression of genes that cause disease. Additionally, recent research on the RNAi effect has shown that administration of particular RNA oligonucleotides could be an especially effective way of silencing genes that are deleterious. Similarly, it has become newly appreciated that DNA oligonucleotides engineered for high affinity binding to particular gene sequences may be useful in gene therapy given the proper delivery system. These kinds of developments make it clear that gene therapy is likely to evolve in a variety of different ways and that different modes will be effective with different diseases.

To date, the primary approach to improving the transfection properties of cationic lipids has been the synthesis of new kinds of cationic amphipaths or the inclusion of non-cationic helper lipids. While such approaches have met with some success, improved transfection reagents that provide efficient transfection (e.g., efficient nucleic acid uptake, low toxicity) are needed.

SUMMARY OF THE INVENTION

Figure 1:
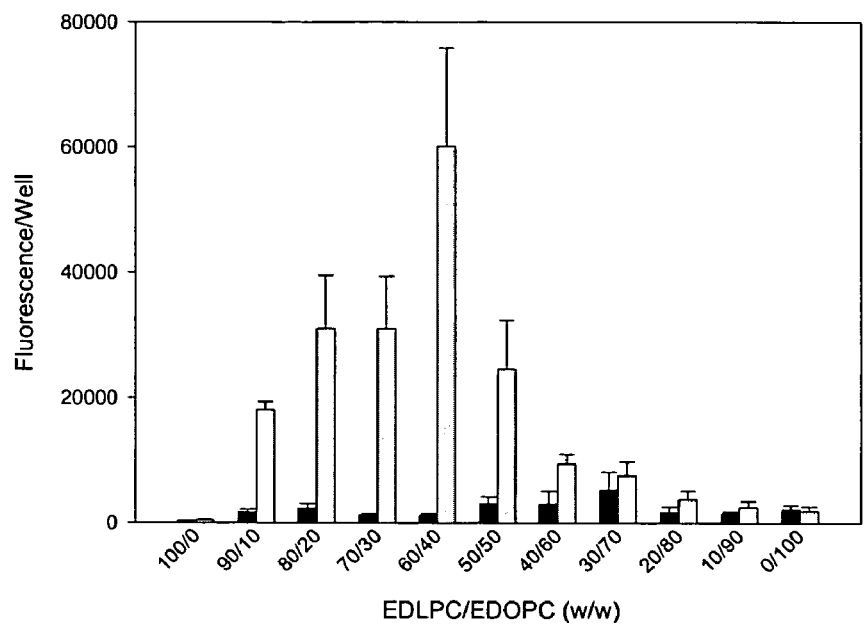
FIG. 1 shows data demonstrating that the extent of transfection of HUAEC varies with the ratio of medium chain to long chain lipids. The cells were seeded in 96-well plates at 24 hours before transfection at densities to give about 80% confluence at the time of transfection. Chloroform solutions of EDLPC with EDOPC and EDLPC with EDMPC were mixed at the different ratios and then chloroform was removed under $N_2$ stream and vacuum. The lipid mixtures were hydrated in HBSS at 1 mg/ml to form liposomes. Liposomes and plasmid DNA were diluted in OptiMEM to 80 μg/ml for lipid and to 20 μg/ml for DNA, and liposomes were pipetted into an equal volume of plasmid DNA solution at a 4:1 weight ratio and mixed gently. The resultant DNA (plasmid with β-galactosidase marker gene)—lipid complexes were incubated at room temperature for 15 min and then added to the cells that were either in medium lacking serum (black bars) or medium containing 5% serum (gray bars). The lipoplexes had 35% (lipoid) excess positive over negative (DNA) charge. Cells were assayed for β-galactosidase expression 24 hours after transfection. Data represent the mean±S.D. of a representative experiment performed in quadruplicate. ~20,000 fluorescence units corresponded approximately to 0.1 milliunit of β-galactosidase.
Figure 1:
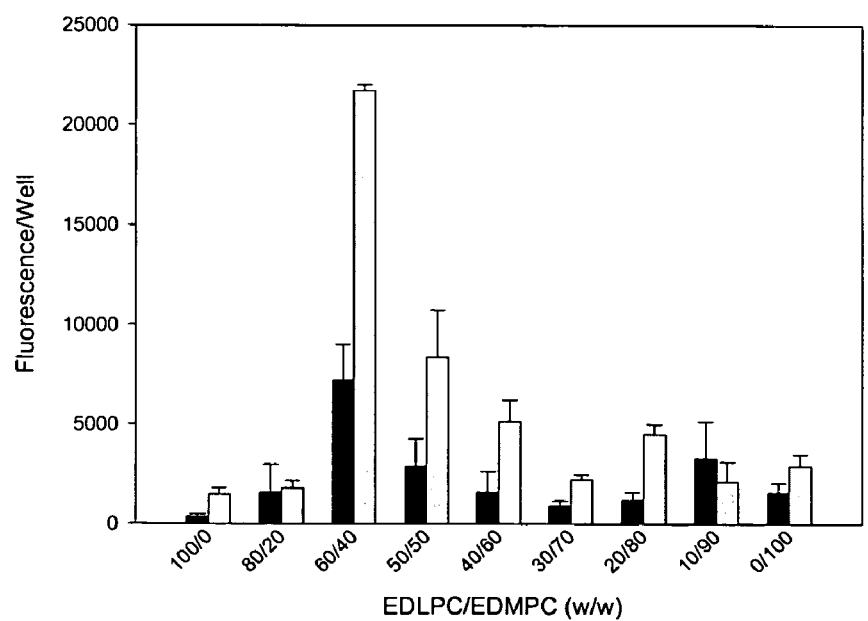

The present invention provides optimized transfection reagents comprising mixtures of, for example, cationic lipids. In some embodiments, the mixture comprises first and second lipids having different fatty acid chains. In some embodiments, the different fatty acid chains comprise fatty acid chains that differ in length (e.g., a first chain having 18 carbons and a second chain having 10, 12 or 14 carbons). The present invention is not limited by the particular lengths or number of fatty chains in the lipids. In some embodiments, the fatty acid chains differ in mean cross-sectional area (i.e., width). The present invention is not limited by the nature of the fatty acid chain constituents that provide difference in cross-sectional area. An example of such a constituent includes, but is not limited to, branches (e.g., methyl branches on the fatty acid chain). In some embodiments, cross-sectional area is altered by mixing a first lipid with a second lipid that differs in that it has a substitution of a long chain fatty acid in a location where such a chain does not normally exist (e.g., substitution of an ethyl group of 1,2-dioleoyl-sn-glycero-3-ethylphosphocholine (EDOPC) to a long chain fatty acid (e.g., stearyl) to provide a mixture of EDOPC and SDOPC).

In some embodiments, the different fatty acid chains are contained in a single molecule (e.g., ethylphosphatidylcholine having an oleoyl and a decanoyl chain). In other embodiments, the different fatty acid chains are present in different molecules in the mixture (e.g., a mixture having 1,2-dioleoyl-sn-glycero-3-ethylphosphocholine (EDOPC) and 1,2-dilauroyl-sn-glycero-3-ethylphosphocholine (EDLPC)).

The present invention is not limited to any particular mechanism of action and an understanding of the mechanism of action is not necessary to practice the present invention. However, it is contemplated that improved transfection is achieved where two or more (e.g., three, four, . . . ) different fatty acid chains are provided in the lipid mixture.

In some embodiments, the mixture comprises first and second cationic lipids. The present invention provides optimized transfection reagents comprising mixtures of cationic lipids. In particular, the present invention provides DNA delivery vehicles based on identifying the optimal hydrophobicity of novel cationic phospholipid derivatives that, alone or in combination, form complexes with DNA (lipoplexes) and exhibit enhanced transfection activity.

In some embodiments, the first cationic lipid is a standard lipid found in transfection reagents. Such standard lipids are those known in the art that are used, for example, to form liposomes (although the present invention is not limited to the use of liposome transfection reagents). Liposomes comprise spheres of lipid bilayers that enclose an aqueous medium. Liposomes can generally be formed by sonicating a lipid in an aqueous medium, by resuspension of dried lipid layers in a buffer or by dialysis of lipids dissolved in an organic solvent or in an aqueous solution against a buffer of choice. Phospholipids form closed, fluid-filled spheres when they are mixed with water, in part because the molecules are amphipathic: they have a hydrophobic (water-insoluble) tail and a hydrophilic (water-soluble), or "polar," head. Two fatty acid chains containing from about 16 up to about 24 carbon atoms generally make up the hydrophobic tail of most naturally occurring phospholipid molecules. Equivalent structures may be employed in synthetic lipids. Phosphoric acid bound to any of several water-soluble molecules composes the hydrophilic head. When a high enough concentration of phospholipids is mixed with water, the hydrophobic tails spontaneously herd together to exclude water, whereas the hydrophilic heads bind to water. In most instances, the result is a bilayer in which the fatty acid tails point into the membrane's interior and the polar head groups point outward. The polar groups at one surface of the membrane point toward the liposome's interior and those at the other surface point toward the external environment. As a liposome forms, any water-soluble molecules that have been added to the water are incorporated into the aqueous spaces in the interior of the spheres, whereas any lipid-soluble molecules added to the solvent during vesicle formation are incorporated into the lipid bilayer. Phospholipid-related materials that are found in typical liposomes include, lecithin, lysolecithin, lysophosphatidylethanolamine, phosphatidylserine, phosphatidylinositol, phosphatidylglycerol, sphinogomyelin, cephalin, cardiolipin, phosphatidic acid, cerebrosides, and ceramide. Some specific examples of phospholipids include, but are not limited to, dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoylphosphatidylethanolamine (POPE), dioleoylphosphatidylethanolamine 4-(N-maleimidomethyl) cyclohexane-1-carboxylate (DOPE-MAL), diheptadecanoyl phosphatidylethanolamine, dilauroylphosphatilylethanolamine, dimyristoylphosphatidylethanolamine, distearoyl phosphatidylethanolamine, beta-linoleoyl-gammapalmitoyl phosphatidylethanolamine and beta-oleoyl-gammapalmitoyl phosphatidylethanolamine). Common cationic lipids found in liposomes include 1,2-diolelyloxy-3-(trimethylamino) propane (DOTAP); N-1-(2,3,-ditetradecyloxy)propyl-N,N-dimethyl-N-hydroxyethylammonium bromide (DMRIE); N-1-(2,3,-dioleyloxy)propyl-N,N-dimethyl-N-hydroxy ethylammonium bromide (DORIE); N-1-(2,3-dioleyloxy) propyl-N,N,N-trimethylammonium chloride (DOTMA); 3α N-(N',N'-dimethylaminoethane) carbamoly cholesterol (DC-Chol); and dimethyldioctadecylammonium (DDAB). Numerous other cationic lipids are known in the art.

In some embodiments, the second cationic lipid is a lipoid with a hydrophobic structure that is significantly different from that of the first lipoid. The present invention is not limited to a particular mechanism. Indeed, an understanding of the mechanism is not necessary to practice the present invention. Nonetheless, the mechanism of action of such a hydrophobic structure may disrupt the packing of the bilayer of a liposome or other structure so that the lipid organization of the array may be different in the mixture, thereby enhancing transfection. Differences in physical organization of lipids of transfection agents may translate into effects on transfection, as measured by detecting transfection efficiency with and without the second cationic lipid or by comparing the transfection reagents having the second cationic lipid to other transfection reagents (see e.g., Example 1 for such a method). Optimization to determine the optimal composition for liposomes or other lipid arrays can be achieved by a variety of methods. For example, in some embodiments, the second cationic lipid has a smaller hydrophobic mass (e.g., shorter hydrophobic tail or net shorter hydrophobic tails in a molecule with multiple tails). In some embodiments, the second cationic lipid is functionalized to add hydrophilicity (e.g., canceling some of the hydrophobic mass). For example, in some embodiments, a lipid head group is made larger or more hydrophilic. In some embodiments, a lipid tail is functionalized to reduce hydrophobicity. For example, in some embodiments, the functionalization comprises addition of one or more polar groups. In some embodiments, a polar fluorophore is added (e.g., NBD), providing the added feature of fluorescent detectability. In some embodiments, the second cationic lipid comprises a head group and a second component with sufficient hydrophobicity to allow it to form a bilayer with the first cationic lipid, but otherwise with low hydrophobicity.

In some embodiments, the first or second lipoids are not cationic. In some embodiments, the second lipid is configured to have shorter acyl chains than a first lipid and/or that alters the packing of the bilayer of a liposome or other structure) as compared to the same structure in the absence of a second cationic lipid (see, e.g., Example 1).

In some embodiments, the present invention provides a composition comprising lipid transfection reagents, wherein the reagents comprise a first cationic lipid (e.g., having a head group and a lipid tail), and a second cationic lipid (e.g., having the same or a different head group and a different, second lipid tail), wherein the second cationic lipid, when combined with said first cationic lipid in said reagents, decreases the hydrophobicity of the reagents compared to said reagents in the absence of the second cationic lipid, and wherein said decrease increases the ability of the reagents to transfect cells. In some preferred embodiments, the second cationic lipid comprises either a short, medium, or long chain fatty acid and the first cationic lipid comprises either a short, medium or long chain fatty acid. A short chain fatty acid is a fatty acid chain having 7 or less carbons. A medium chain fatty acid is a fatty acid chain having between 8 and 15 carbons (e.g., laurate, myristate, etc.). A long chain fatty acid is a fatty acid chain having 16 or more carbons (e.g., palmitate, stearate, oleate, etc.). The lipid tails may be saturated or unsaturated.

In other embodiments, the second lipid has lipid tails that may be the same length as those of the first lipid, but are of a different shape. Such different shapes arise by incorporating different carbon chain branches along the lipid tails (e.g., as when methyl branches are incorporated along the lipid tail, the result of which is to increase the cross-sectional area (in the plane of the bilayer) of the lipid). Generally, the chains may be either shorter and/or fatter than the chains of the first lipid.

The cationic lipids of the present invention may be of any form, including, but not limited to, natural or synthetic lipoids having head groups with one or more (e.g., two) fatty acyl or alkyl chains attached. Where more than one fatty chain is provided on a lipid molecule, the chains may be the same or different. In some embodiments, the modified bilayer structure is achieved by lengthening one of the two tails and shortening the other. In some embodiments, the shortened chain is reduced in size more than the lengthened chain is increased. In some embodiments, the two chains are of similar length, but of different cross sectional area. In some embodiments, the lipid does not comprise a traditional head group/tail structure. For example, in some embodiments, cationic cholesterol derivatives or similar structures may be used. In some embodiments, the cationic lipids comprise any type of head group, including, but not limited to, chemically modified phosphatidylcholine, phosphatidylethanolamine, phosphatidylglycerol, phosphatidylinositol, phosphatidylserine, and sphingomyelin, and derivative thereof. In some preferred embodiments, the first cationic lipid comprises a dioleoyl O-ethylphosphatidylcholine. In some preferred embodiments, the second cationic lipid comprises a dilauroyl O-ethylphosphatidylcholine. The present invention is not limited by the ratio of the first and second cationic lipids within the composition. In some embodiments, the composition further comprises one or more additional components such as cholesterol or other lipids. In some embodiments, the composition further comprises a nucleic acid molecule (e.g., a vector, naked DNA, antisense oligonucleotides, siRNA, etc.), a protein, a small molecule drug, or other desired agents.

The present invention also provides methods for transfecting cells. In some embodiments, the method comprises exposing a cell to the composition described above, wherein the composition comprises a nucleic acid molecule. The cell may reside in vitro (e.g., in culture), ex vivo, or in vivo. The cell may be isolated or may be associated with other cells (e.g., in a tissue).

Definitions

To facilitate an understanding of the present invention, a number of terms and phrases are defined below:

As used herein the term "lipid" refers to any natural or synthetic lipid molecules, including non-natural compounds that are similar to lipids in structure and properties (e.g., they are amphipaths).

As used herein the term "transfection efficiency" refers to, for example, the percentage of target cells, within a population of target cells, that contain an introduced exogenous nucleic acid molecule. Transfection efficiency can be determined by transfecting a nucleic acid molecule encoding a reporter gene into a population of target cells and determining the percentage of cells having reporter activity. The term "transfection efficiency" also refers to the amount of gene product detected following transfection of the nucleic acid into the cell. This is determined, for example, by testing an entire cell population for the amount of gene product produced after a given incubation period. Thus, the term "transfection efficiency" involves assaying for the relative expression of the gene product encoded by the introduced nucleic acid.

As used herein, the term "liposome" refers to a vesicle bounded by a lipid bilayer. A "cationic liposome" has a net positive charge.

As used herein, the term "short chain fatty acid" refers to a fatty acid chain having 7 or less carbons.

As used herein, the term "medium chain fatty acid" refers to a fatty acid chain having between 8 and 15 carbons (e.g., laurate, myristate, etc.).

As used herein, the term "long chain fatty acid" is a fatty acid chain having 16 or more carbons (e.g., palmitate, stearate, oleate, etc.).

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1.alpha. gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous"

or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables).

DESCRIPTION OF THE INVENTION

The present invention provides an alternative approach to improving transfection reagents. The compositions and methods of the present invention were shown to be unusually effective. In preferred embodiments, the present invention provides the combination of two or more cationic lipids to provide improved transfection reagents. In some embodiments, the first cationic lipid is a standard cationic lipid used in transfection reagents and the second cationic lipid is of the nature where, when combined with the first cationic lipid in transfection reagents, alters the hydrophobicity of the hydrophobic mass either in the extent of hydrophobicity of the lipoids or in the organization of the lipoids compared to the reagents in the absence of the second cationic lipid, and wherein such change in hydrophobicity increases the ability of the transfection reagents to transfect cells.

In some embodiments, the second cationic lipoid is a lipoid that has higher water solubility than the first lipoid and/or that increases the exposure of the hydrophobic core of the lipoid structure to an aqueous environment (e.g., disrupt the bilayer of a liposome) as compared to the same structure in the absence of the second cationic lipoid. The degree of increase in water solubility and/or increased exposure of the hydrophobic core that finds use in the present invention can readily be measured by detecting transfection efficiency with and without the second cationic lipoid or by comparing the transfection reagents having the second cationic lipoid to other transfection reagents (see e.g., Example 1 for such a method). Optimization to increase water solubility and/or increased exposure of the hydrophobic core can be achieved by a variety a methods. For example, in some embodiments, the second cationic lipoid has a smaller hydrophobic mass (e.g., shorter hydrophobic tail). In some embodiments, the second cationic lipoid is functionalized to add hydrophilicity (e.g., canceling some of the hydrophobic mass). In some embodiments, the functionalization comprises addition of one or more polar groups. In some embodiments, a polar fluorophore is added (e.g., NBD), providing the added feature of fluorescent detectability.

For example, particularly efficient transfection reagents were produced by the combination of dilauroyl (12 carbon chain) and dioleoyl (18 carbon chain) homologues of O-ethylphosphatidylcholine. This mixture transfected DNA into human umbilical artery endothelial cells (HUAECs) more than 30-fold more efficiently than either compound separately. A unique advantage of this kind of combination agent is that transfection can be optimized either in the presence or absence of serum by adjusting the component ratio.

In some embodiments, the second lipoid has chains that are not significantly different in length from those of the first lipoid, but the second lipoid has chains that have a larger cross-sectional area.

In some embodiments, the second lipoid has chains that are differently shaped from those of the first lipoid, so as to occupy space in the bilayer in a different way than those of the first lipoid.

Cationic lipids have been widely used for the delivery of plasmid and antisense DNA into eukaryotic cells; however, inefficiency of transfection is a major problem confronting their use in gene therapy. Vascular endothelial cells act as an interface between circulating blood and various tissues and organs of the body, and are known to be involved in inflammatory processes such as leukocyte recruitment, cytokine production (see, e.g., Koning G A, et al., *Endothelium* 2002; 9:161-171; Neuhaus T et al., *Clinical Science* 2000; 98: 461-470; Stier S et al., *FEBS Letters* 2000; 467: 299-304; each herein incorporated by reference in their entireties), and to play a major role in the pathogenesis of atherosclerosis (see, e.g., Behrendt D, and Ganz P., *Am J Cardiol* 2002; 90: 40L-48L; Ulrich-Merzenich G, et al., *European Journal of Nutrition* 2002; 41: 27-34; each herein incorporated by reference in their entireties), as well as angiogenesis (see, e.g., Ellis L M. *Am Surg* 2003; 69: 3-10; Nam N H, Parang K. *Curr Drug Targets* 2003; 4: 159-179; Ranieri G, and Gasparini G., *Curr Drug Targets Immune Endocr Metabol Disord* 2001; 1: 241-253; Sylven C. *Drugs Today (Barc)* 2002; 38: 819-827; each herein incorporated by reference in their entireties), on which the growth and spread of tumors are dependent. Hence, they are of considerable interest as a gene therapy target (see, e.g., Baker AH., *J Card Surg* 2002; 17: 543-548; Morishita R., *Circ J* 2002; 66: 1077-1086; each herein incorporated by reference in their entireties). Even though they are readily accessible, gene therapy with nonviral vectors of endothelial tissue has been seriously hampered by the fact that endothelial cells are very difficult to transfect. According to Struck et al., Biochemistry 1981, 20:4093-4099, the transfection efficiency of vascular endothelial cells with cationic lipids was only 2%. It is known that the cytotoxicity of cationic lipids increases with the shortening of acyl groups and so cationic lipids used in transfection invariably have alkyl chains that are 14 or more carbon long. The present invention provides solutions to such problems.

For example, in one embodiment, a short chain cationic phosphocholine (1,2-dilauroyl-sn-glycero-3-ethylphosphocholine, EDLPC), when combined with longer chain compounds (1,2-dioleoyl-sn-glycero-3-ethylphosphocholine, EDOPC, or 1,2-dimyristol-sn-glycero-3-ethylphosphocholine, EDMPC) dramatically enhances (up to 30-fold) the transfection efficiency of human umbilical artery endothelial cells (HUAECs) even though, individually, EDLPC, EDOPC or EDMPC are quite weak transfection reagents. Moreover, transfection efficiency can be adjusted to be optimal either in the presence or absence of serum by changing the EDLPC/EDOPC ratio and the ratio of total lipids to DNA. Under optimal conditions, transfection efficiency can be achieved up to 15% both in the presence and absence of serum. Thus, these formulations constitute a novel form of cellular transfection reagent and offer entirely new formulations for optimizing in vivo gene delivery. At present, only phosphatidylethanolamine and cholesterol are used as the helper lipids to improve the transfection properties of cationic lipids. Unlike these prior methods (although they may be used in conjunction with the present invention), the present invention employs compounds with different hydrophobicity-hydrophilicity balance to improve the gene delivery properties of lipoplexes. The properties of lipoplexes can be tuned by changing the ratio of the different lipoids (e.g., the ratio of medium chain to long chain cationic lipids and the ratio of lipid to DNA).

In some preferred embodiments, one or more agents may be added to the cationic lipid mixtures so as to further increase transfection efficiency. Examples of agents include, but are not limited to, cholesterol, polyamidoamine dendrons, histidylated lipids, octylglucoside, phycoerythrin, and non-cationic lipids. In some preferred embodiments, the cationic lipid mixtures may be transfected with additional transfection reagent systems so as to further increase transfection efficiency. Examples of transfection reagent systems include, but are not limited to, LIPOFECTAMINE (Invitrogen), OPTIFECT (Invitrogen), 293FECTIN (Invitrogen), OLIGOFECTAMINE (Invitrogen), CELLFECTIN (Invitrogen), LIPOFECTIN (Invitrogen), DMRIE-C (Invitrogen), EXGEN 500 (Euromedex), octylglucoside, FUGENE (Roche), EFFECTGENE (Qiagen), and SUPERFECT (Qiagen).

In some embodiments, the first or second lipoids are not cationic but are configured to have a structural impact on the bilayer into which they are incorporated (e.g., to impact the water solubility than a cationic lipid used alone, to increase the exposure of the hydrophobic core of the lipoid structure to an acqueous environment, or to disrupt the packing of the bilayer of a liposome or other structure as compared to the same structure in the absence of a second cationic lipoid).

Transgenes

The transfection system described herein is useful to express any polypeptide of interest or to transfect any nucleic acid of interest (e.g., siRNAs, antisense oligonucleotides, expression vectors, etc.).

The transgene will generally encode a native or recombinant protein, although the expression of other polypeptides, such as epitopes or other immunologically active polypeptides, are contemplated within the scope of this invention. Examples of proteins that can be expressed using the method of the present invention are hormones; cytokines, such as growth factors; enzymes; receptors; oncogenes; polypeptide vaccines, viral proteins, and structural and secretory proteins.

The transgene employed in the constructs of the invention can be cloned sequences that retain intronic regions. If the exonic structure of the gene is known, the coding exons can be inserted in the constructs.

Expression of the polypeptide of interest can be directed by a promoter homologous to the polypeptide coding sequences (for example, human glucose-6-phosphate dehydrogenase under the control of its own transcription promoter sequences). Further, other homologous or heterologous expression control elements (e.g., affecting transcription, translation, or post-translational events) may be used.

It should be understood that expression of the transgene in the mammalian cells of the invention can be stable or transient. Even transient expression, at a higher than normal level, is useful for functional studies in the cells or for the production and recovery of proteins of interest.

Regulatory Sequences

In addition to selectable markers and transgenes, the constructs described herein may contain suitable regulatory elements. Regulatory elements (or control elements) are selected for use in the host cell of interest; for example, selectable markers may be included to allow propagation in microorganisms, (e.g., f1 origin of replication and ampicillin resistance encoding sequences). Such regulatory elements include, but are not limited to, transcription promoters, transcription enhancer elements, transcription termination signals, polyadenylation sequences (located 3' to the translation stop codon), sequences for optimization of initiation of translation (located 5' to the coding sequence), translation termination sequences, secretion signal sequences, and sequences that direct post-translational modification (e.g., glycosylation sites). Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

Cells

The cells (e.g., host cells) employed in this invention include all eukaryotic cells including mammalian cells (in vivo or in vitro), cell lines, and cell cultures. The cells can be derived from mammals, such as mice, rats, or other rodents, or from primates, such as humans or monkeys. Mammalian germ cells or somatic cells can be employed for this purpose. It will be understood that primary cell cultures or immortalized cells can be employed in carrying out the techniques of the present invention. The cells may also reside in vivo. Examples of cells used in the present invention include, but are not limited to, HUAAEC cells, human dermal fibroblast cells, cancer cells (e.g., myeloma cells).

The transformed cells obtained by some embodiments of the present invention can be employed for the preparation of continuous cell lines in which the cells are essentially immortal, or for the preparation of established cell lines that have the potential to be subcultured in vitro. Continuous cell lines and established cell lines can be obtained from a variety of organisms and organs, such as rodent embryos; primate kidneys; rodent and human tumors; and fibroblast, epithelial, or lymphoid cells. Cells exhibiting the highest levels of expression can be cloned, if desired.

EXAMPLES

The following examples are provided to demonstrate and further illustrate certain preferred embodiments of the present invention and are not to be construed as limiting the scope thereof.

Example 1

EDLPC/EDOPC Transfection Reagents

Experiments conducted during the development of the present invention found that attention to the hydrophobic portions of medium and long-chain cationic lipids synergistically enhance transfection. It was found that a combination of two cationic lipid derivatives with the same head group but tails of different chain lengths behave considerably differently as transfection agents than the separate molecules. For example, the combination of the dilauroyl (12 carbon chain) and the dioleoyl (18 carbon chain) homologues of O-ethylphosphatidylcholine transfected DNA into primary human umbilical artery endothelial cells (HUAECS) more than 30-fold more efficiently than either compound separately. The present invention is not limited to a particular mechanism. Indeed, an understanding of the mechanism is not necessary to practice the present invention. Nonetheless, these results suggest that the hydrophobic portions of medium and long-chain cationic lipids is far more important than previously assumed. An advantage of this kind of combination agent is that transfection is optimized either in the presence or absence of serum by adjusting the component ratio.

Considering that there are more opportunities to modify and combine the hydrophobic moieties on cationic lipids than there are for variation of the head groups, a study of the transfection efficiency of lipids with different kinds of tails and different kinds of combinations of those tails leads to new and improved nonviral vectors was conducted. A unique advantage of the cationic phospholipoids for hydrophobic structure modification is that they allow use of specific enzymes in their synthesis, a feature not exhibited by the other cationic lipids described in the literature because those compounds are not based on a natural product.

FIG. 1 shows that combining EDLPC with EDOPC enhances by ~30-fold of the extent of transfection of HUAECS, compared to EDLPC or EDOPC alone. The ratio of EDLPC to EDOPC affected performance, with different ratios optimal, depending upon whether serum is present or absent. The EDLPC/EDMPC mixture exhibits the similar pattern to that of EDLPC/EDOPC, but the extent of transfection is lower than that of EDLPC/EDOPC.

Figure 2:
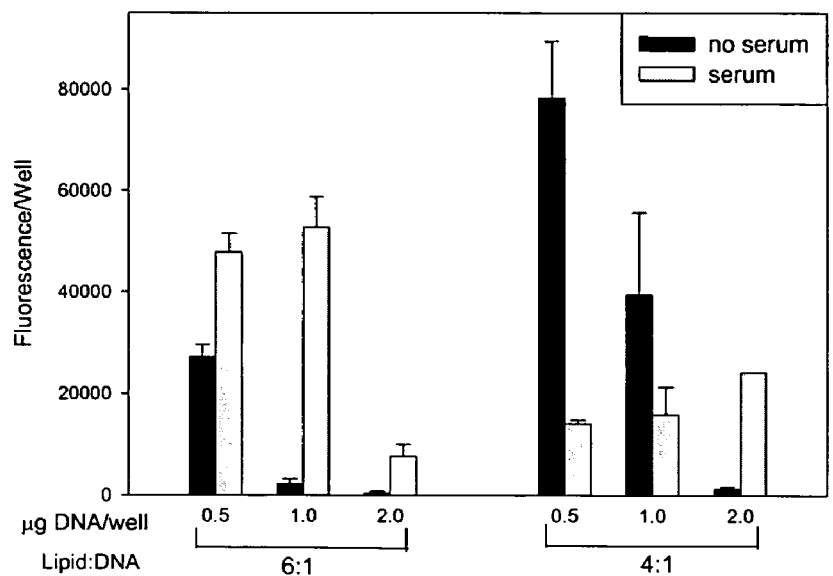
FIG. 2 shows data demonstrating the change of transfection with the ratio of EDLPC to EDOPC and the ratio of total lipids to DNA. Cells were treated with DNA-lipid complex for 2 h in the absence ("no serum") or presence of serum ("serum") and then washed with HBSS and supplemented with fresh culture medium. Data represent the mean±S.D. of a representative experiment performed in quadruplicate.
Figure 2:
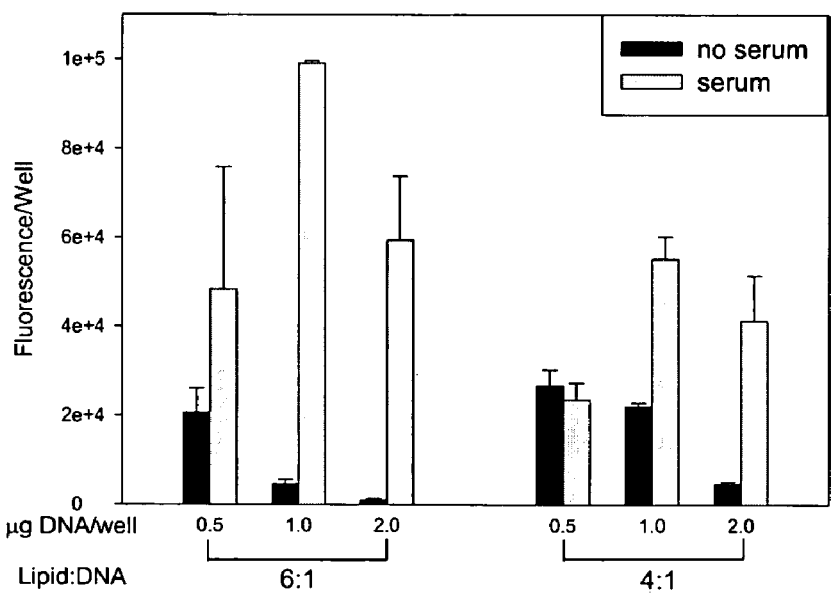

On the basis of the results presented above, EDLPC/EDOPC (80/20) and EDLPC/EDOPC (60/40) were chosen to further optimize transfection; the ratio of lipids to DNA and the amount of DNA were used as optimization parameters. FIG. 2 depicts the change of transfection with the ratio of EDLPC to EDOPC and the ratio of total lipids to DNA. For some formulations, transfection without serum was better than that in serum; but for others, transfection in serum was better than that in the absence of serum. The highest transfection in the absence of serum was obtained when EDLPC/EDOPC=80/20 and lipid/DNA=4/1, with 0.5 µg DNA/well; under these conditions the extent of expression was 8× higher than that in the presence of serum. In contrast, the most efficient transfection in the presence of serum was when EDLPC/EDOPC=60/40 and lipid/DNA=6/1, with 1.0 μg DNA/well, under which condition the expression was 20× that in the absence of serum. According to X-gal staining, 15% of the cells treated under both of these conditions were positive. This efficiency of transfection is more than an order of magnitude higher than has been previously reported for transfection of these primary cells. These two formulations were thus used in the subsequent studies. Such assays can be used to readily determine optimal ratios and optimal components of the transfection reagents of the present invention.

The cell viability and the percentage of cells transfected for the two formulations were determined using the MTT method and X-gal staining, respectively (Table 1). Those data revealed that the low transfection efficiency in the absence of serum for EDLPC/EDOPC=60/40 and lipid/DNA=6/1 was due to high cytotoxicity.

While the present invention is not limited to any particular mechanism of action and an understanding of the mechanism of action is not necessary to practice the present invention, it is contemplated that the medium chain lipid facilitates mixing of the lipoplex lipid with cellular lipid, which could lead to the neutralizing of the positive charge of the cationic lipid and facilitate release of DNA from the complex. Under such circumstances, EDLPC could facilitate fusion (or at least lipid mixing) of cationic liposomes with anionic liposomes.

Figure 3:
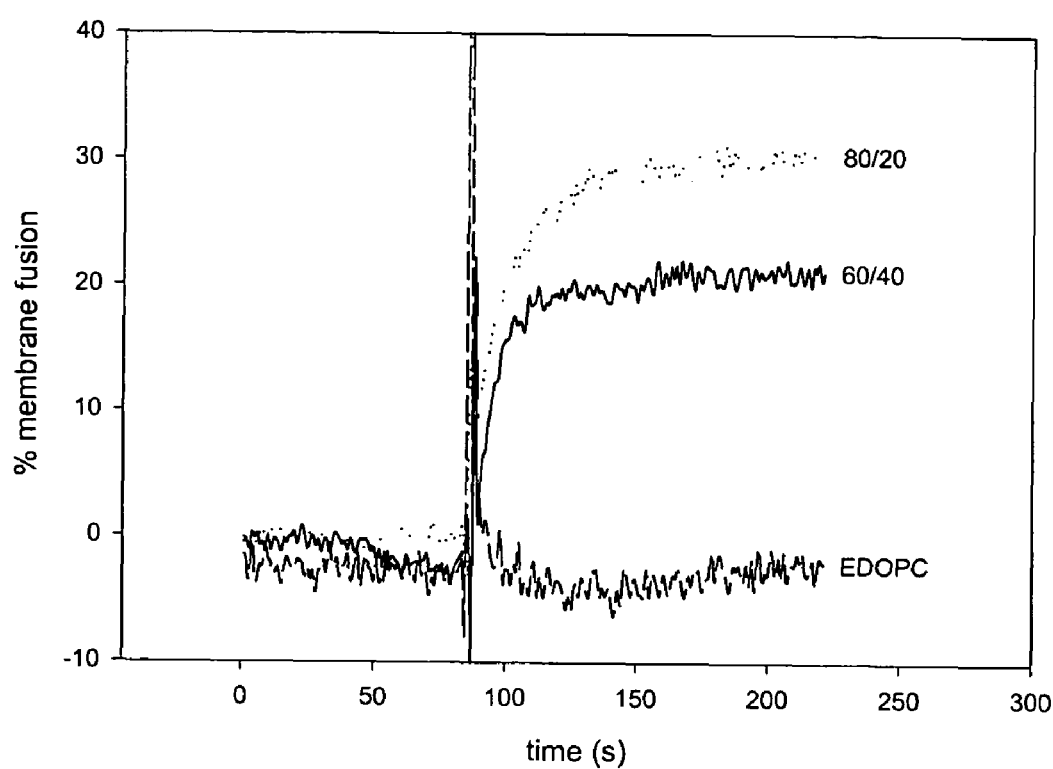
FIG. 3 shows a graph of the membrane fusion of fluorescence-labeled, cationic lipoplexes with anionic liposomes. The lipids were labeled with 0.5 mol % each of NBD-PE and Rh-PE and hydrated at 1 mg/ml in PBS. Lipoplexes were then prepared as for transfection. Two hundred microliters of the resulting lipoplexes were titrated with 3-fold mol unlabeled egg PC liposomes containing 20% DOPG. The experiments were done at 37° C. Ex=320 nm, Em=535 nm. % membrane fusion=$(F_n-F_0)/(F_{100}-F_0) \times 100\%$, where $F_n$ is the fluorescence after the addition of anionic lipid, $F_0$ is the initial fluorescence of lipoplexes, and $F_{100}$ is the fluorescence when anionic lipid was mixed directly with cationic lipids in chloroform and then lipoplexes were prepared as above.

The fusion of EDLPC/EDOPC (80/20), EDLPC/EDOPC (60/40) and pure EDOPC lipoplexes were compared to phosphatidylglycerol-containing (anionic) liposomes. Membrane fusion was measured using a FRET assay (see, e.g., Struck D K, et al., *Biochemistry* 1981; 20: 4093-4099; herein incorporated by reference in its entirety) that measures reduction of energy transfer between NBD-PE and Rh-PE in cationic lipids of the lipoplexes as they fuse with egg-PC liposomes containing 20% DOPG. From FIG. 3, it is seen that the extent of fusion of EDLPC/EDOPC (80/20) and EDLPC/EDOPC (60/40) lipoplexes is significantly higher than that of pure EDOPC. The present invention is not limited to a particular mechanism. Indeed, an understanding of the mechanism is not necessary to practice the present invention. Nonetheless, these results indicate that increased transfection efficiency is associated with membrane fusion characteristics.

Figure 4:
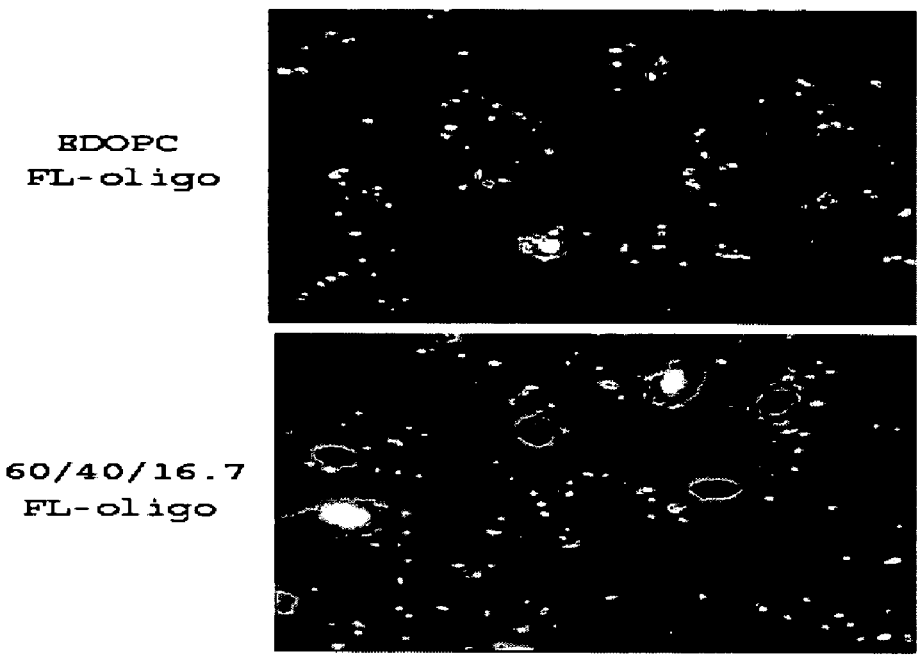
FIG. 4 shows oligonucleotide distribution of EDOPC and EDLPC/EDOPC/DNA (60/40/16.7) lipoplexes in HUAECs. Lipoplexes were labeled with a fluoresce in derivative of a double-stranded dodecameric oligonucleotide. Cells were incubated with the resulting lipoplexes in the presence of serum for 2 h and imaged under a fluorescence microscope at 2 h later after being washed with HBSS.

In order to determine if this pattern of fusion is also observed within cells (e.g., the mixture is more prone to fuse with endosomal membranes facilitating escape of DNA from endosomal degradation and nuclei entrance) the intracellular distribution of fluorescent lipid and oligonucleotide in EDOPC and EDLPC/EDOPC (60/40) lipoplexes was investigated. It was found that both lipid and oligonucleotide in EDOPC lipoplexes remained in the cytoplasm for at least 20 hours, whereas a large amount of the oligonucleotide from EDLPC/EDOPC (60/40) lipoplexes entered the nuclei, in particular at the early time point of 2 h, although lipid in EDLPC/EDOPC (60/40) lipoplexes remained in the cytoplasm at this and all other time points. FIG. 4 shows oligonucleotide distribution of EDOPC and EDLPC/EDOPC/DNA (60/40/16.7) lipoplexes in HUAECSs. Lipoplexes were labeled with a fluorescein derivative of a double-stranded dodecameric oligonucleotide. Cells were incubated with the resulting lipoplexes in the presence of serum for 2 h and imaged under a fluorescence microscope after being washed in HBSS. As shown in FIG. 4, the results of these experiments indicated that in the presense of the lipid mixture there was an increase in the nuclear distribution of highly fluorescent oligonucleotides. Similar images were obtained with fluorescent plasmid DNA, although the fluorescence of the nucleus was less intense.

Escape of lipoplexes from endosomes prior to their entry into lysosomes is important for transgene efficient expression. It is contemplated that fusion of lipoplexes with endosomal membranes facilitates DNA release from endosomes into cytoplasm, and thus increase DNA expression. While the present invention is not limited to any particular mechanism of action and an understanding of the mechanism of action is not necessary to practice the present invention, it is contemplated that this may be one reason that transfection by the mixtures of lipid is much higher than that of pure EDOPC.

The present invention is not limited to a particular mechanism. Indeed, an understanding of the mechanism is not necessary to practice the present invention. Nonetheless, it is contemplated that dissociation of DNA from the surface of a lipid is caused by neutralization of the lipid by cellular anionic lipids. Such neutralization implies fusion or transfer of lipids as a necessary prerequisite of efficient transfection, and implies that the DNA must become sufficiently free of the lipid-lipoid array to be transcribed in the nucleus. Unlike normal cellular lipids, the combination of cationic lipids and anionic lipids gives rise to a variety of non-lamellar phases which may or may not be capable of retaining a molecule as large as a typical plasmid. Generally, generation of lipid phases through combination of cationic and anionic lipids is dependent upon lipids (see, e.g., Tarahovsky, Y. S., et al., 2004, Biophysical Journal 87:1054-1064; herein incorporated by reference in its entirety). For example, mixtures such as EDOPC-EDLPC, when reconstituted with anionic lipids such as phosphatidylglycerol, give rise to a highly curved inverted micellar cubic phase. This phase is characterized by a cubic array of balls (shells) in which amphipathic molecules are organized with their polar portion facing a small aqueous core and their hydrophobic tails facing those of other shells. These phases have aqueous spaces too small to entrap either a plasmid or other DNA molecule. Separate experiments have revealed that treatment of EDOPC-EDLPC lipoplexes with the anionic lipid, phosphatidylserine, releases more DNA by far that does treatment of EDOPC lipoplexes with phoshatidylserine. The present invention is not limited to a particular mechanism. Indeed, an understanding of the mechanism is not necessary to practice the present invention. Nonetheless, it is contemplated that there are at least two important effects involved when certain kinds of lipid mixtures are used to prepare lipoplexes. First, the mixed lipoid lipoplex may acquire anionic lipid from the cell (e.g., perhaps by membrane fusion or molecular exchange) faster and/or to a larger extent than do lipoplexes composed of lipoids of a single type. Second, the phase or 3-dimensional array assumed after the cellular anionic lipid and the lipoplex lipid may have such a structure as to release faster and/or to a greater extent its cargo of DNA than do conventional lipoplexes.

Figure 5:
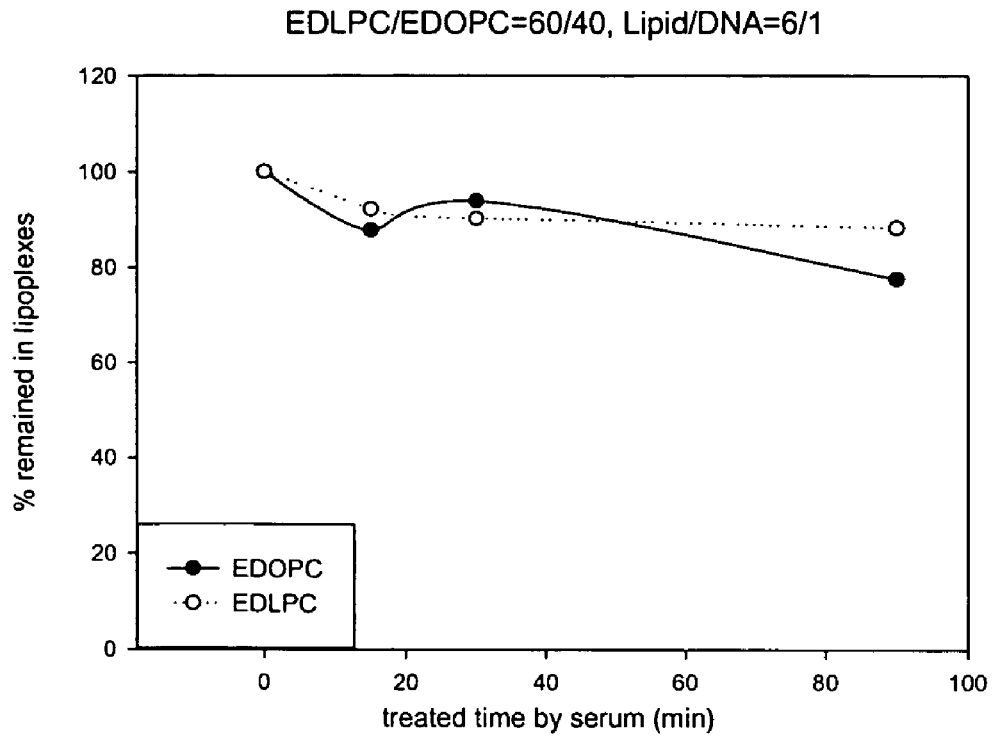
FIG. 5 shows graphs showing the effect of serum on the composition of lipoplexes. Lipoplexes were treated with 5% serum at 37° C. for different times, and centrifuged at 14,000 rpm (4° C.) for 1 h. The pellets were collected and extracted with chloroform. The chloroform phase was applied to a TLC plate, which was then developed in chloroform/methanol/ $H_2O$ (65:25:4). The separated EDLPC and EDOPC were obtained by extracting $SiO_2$ of the relevant regions of the TLC plate with chloroform/methanol/$H_2O$ (10:10:1). EDLPC and EDOPC were quantified with a phosphate assay.
Figure 5:
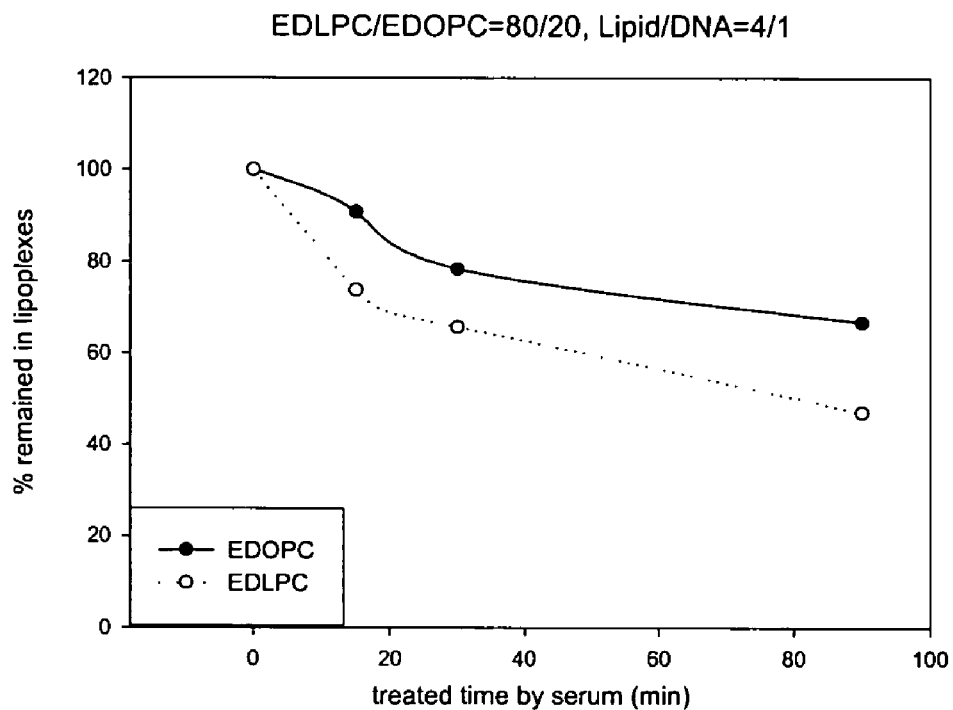

Serum strongly influences properties of lipoplexes, so experiments were conducted to examine the effect of serum on the composition of these two formulations. In FIG. 5, one sees that during 90 min incubation in serum, for EDLPC/EDOPC=60/40, 20% of the EDOPC and 10% of the EDLPC were extracted from the lipoplexes; in the case of EDLPC/EDOPC=80/20, 30% of the EDOPC and 50% of the EDLPC are extracted. Furthermore, at early times (30 min), which are contemplated to be more important for endocytosis, the extraction of EDLPC and EDOPC from EDLPC/EDOPC=80/20 was much larger than that from EDLPC/EDOPC=60/40.

Figure 6:
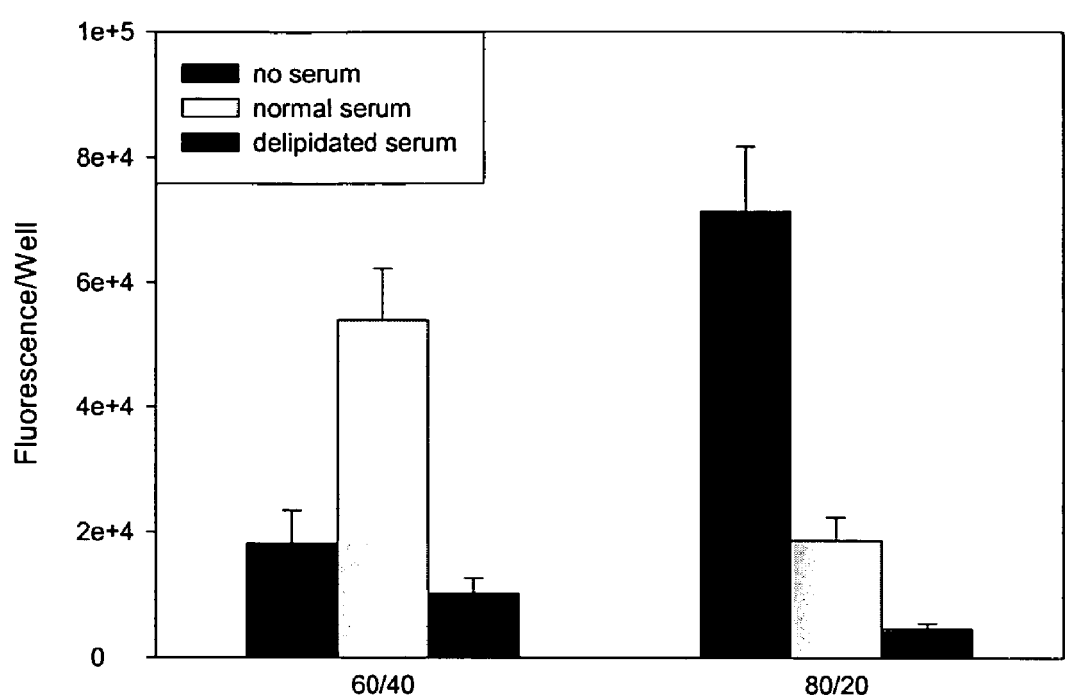
FIG. 6 shows a graph showing the effect of serum on the transfection of HUAEC. Cells were treated with DNA-lipid complex for 2 h in the absence ("no serum") or presence of 5% normal serum ("normal serum") or 5% delipidated serum ("delipidated serum") and then washed with HBSS and supplemented with fresh regular culture medium. Data represent the mean±S.D. of a representative experiment performed in quadruplicate.

Gene expression in delipidated serum was tested (FIG. 6). Transgene expression of both two formulations decreased significantly in delipidated serum, in which ~80% lipids (including cholesterol, HDL cholesterol, LDL cholesterol and phospholipids) are absent relative to normal serum. While the present invention is not limited to any particular mechanism of action and an understanding of the mechanism of action is not necessary to practice the present invention, it is contemplated that this indirectly confirms serum extraction of lipids, since delipidated serum, with a higher lipid binding capacity than normal serum, would also extract more lipids from the lipoplex.

Human dermal fibroblasts are another medically important cell type through participation in wound healing. It was contemplated that human dermal fibroblasts would be useful in gene therapy to accelerate wound healing. It was therefore of interest to determine if the "mixed lipid" effect also operates in these primary cells. It was found that the "mixed lipid" effect is more pronounced than with HUAECs. The response in serum was not as pronounced, but efforts were not made to optimize the conditions for this system.

A human multiple myeloma cell line that is extremely difficult to transfect was also investigated and the "mixing effect" was observed, although the transfection efficiency was very low (1-2%).

Figure 7:
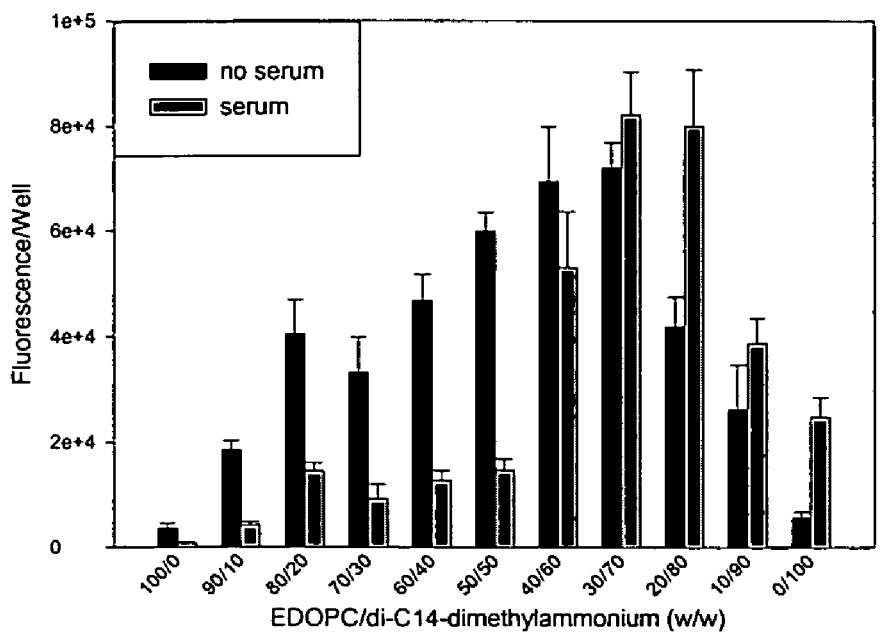
FIG. 7 shows a mixed lipid effect in transfection with tetraalkylammonium compounds. Conditions were identical with those described in FIG. 1 except that different lipid mixtures were used. Ditetradecyldimethyammonium (di C 14 substituted quaternary ammonium) was mixed with dioctadecylammonium (di C 18 quaternary ammonium).
Figure 7:
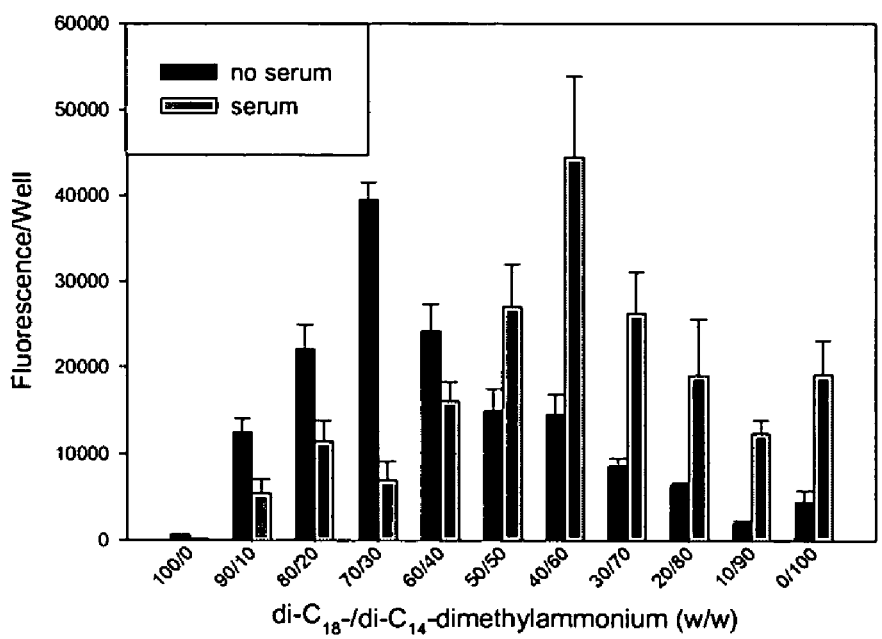

The mixed lipid effect is not limited to cationic phospholipids. As shown in FIG. 7, the effect is seen when a dimethylammonium with two C14 chains is mixed with EDOPC and when the C 18 phospholipoid is replaced with a dimethylammonium having two C 18 chains. The TAP compounds, DOTAP and DMTAP in various combinations, were investigated with each other and with EDOPC. In all cases substantial increases at intermediate compositions was observed. The present invention is not limited to a particular mechanism. Indeed, an understanding of the mechanism is not necessary to practice the present invention. Nonetheless, the mixed lipid effect appears quite general, as would be anticipated if some aspect of the hydrophobicity of the lipoplex needs to be matched to the cell and the transfection conditions. Although other lipids can be synthesized to have chain length differences, it is unlikely that any other such compounds offer the flexibility of structural variation as the cationic phospholipoids. Thus, while the present invention is not limited to the use of cationic lipids, cationic lipids are a preferred material. These compounds offer enormous flexibility in constructing molecules with varied amount and configuration of hydrophobic moieties.

Example 2

Figure 8:
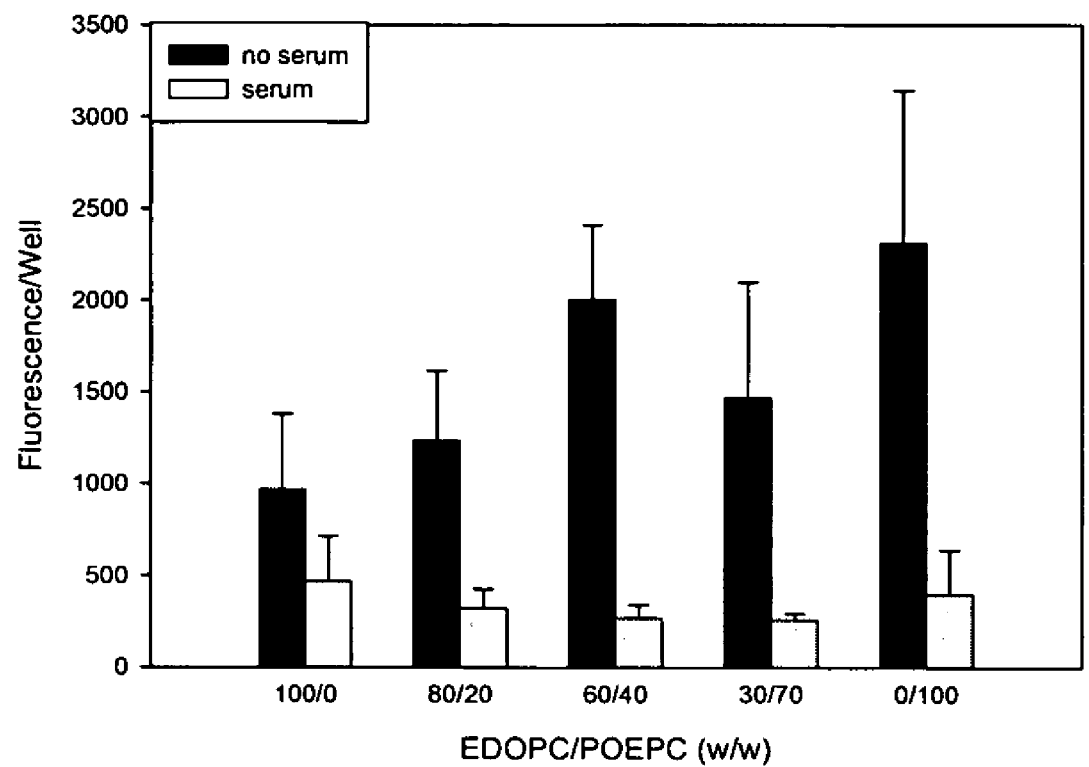
FIG. 8 shows the results of transfecting human dermal fibroblast cells with EDOPC/EPOPC (one oleoyl chain, which is 18C's with one double bond, and one palmitoyl, which is 16C's without double bond) mixtures.

Transfection of Human Dermal Fibroblasts with EDOPC/EPOPC and EDOPC/EDiphytanoyl PC Transfection Reagents FIG. 8 shows that combining EDOPC with EPOPC (one oleoyl chain, which is 18C's with one double bond, and one palmitoyl chain, which is 16C's without any double bond) shows little mixing effect in transfection of human dermal fibroblast cells in the absence of serum.

Figure 9:
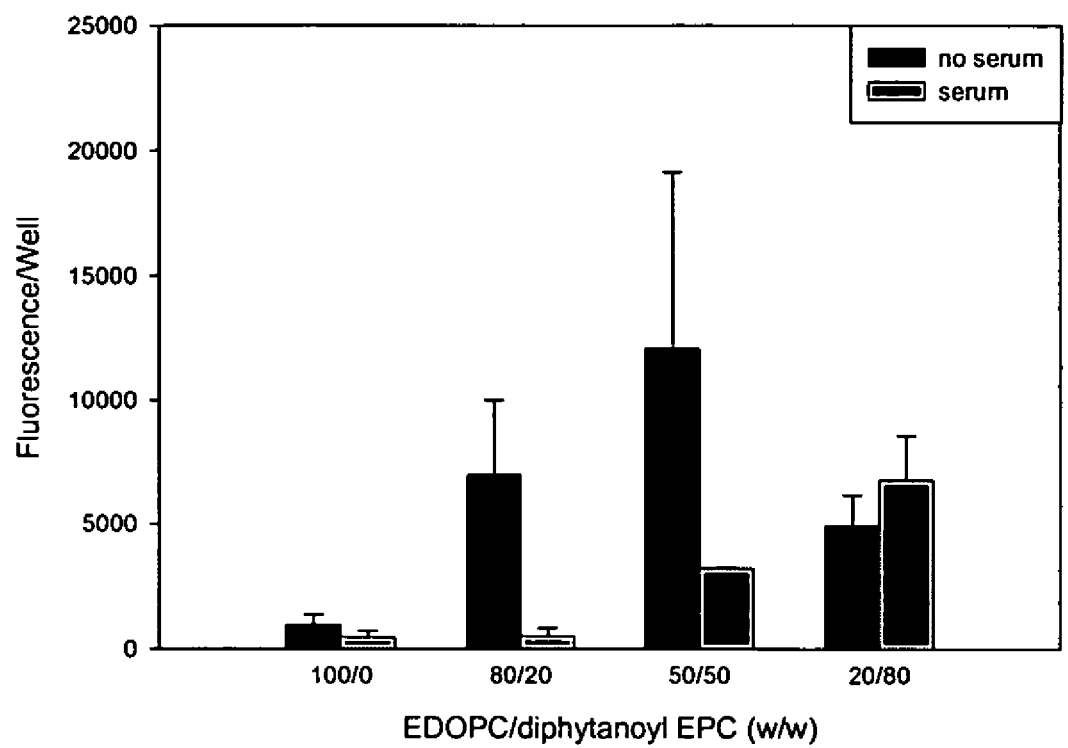
FIG. 9 shows the results of transfecting human dermal fibroblast cells with EDOPC/EDiphytanoyl PC (two phytanoyl chains, 16 carbon chains with 4 methyl branches) mixtures.

FIG. 9 shows that combining EDOPC with EDiphytanoyl PC (two phytanoyl chains, 16 carbon chains with 4 methyl branches) shows marked mixing effect in the transfection of human dermal fibroblast cells in the absence of serum.

Example 3

Figure 10:
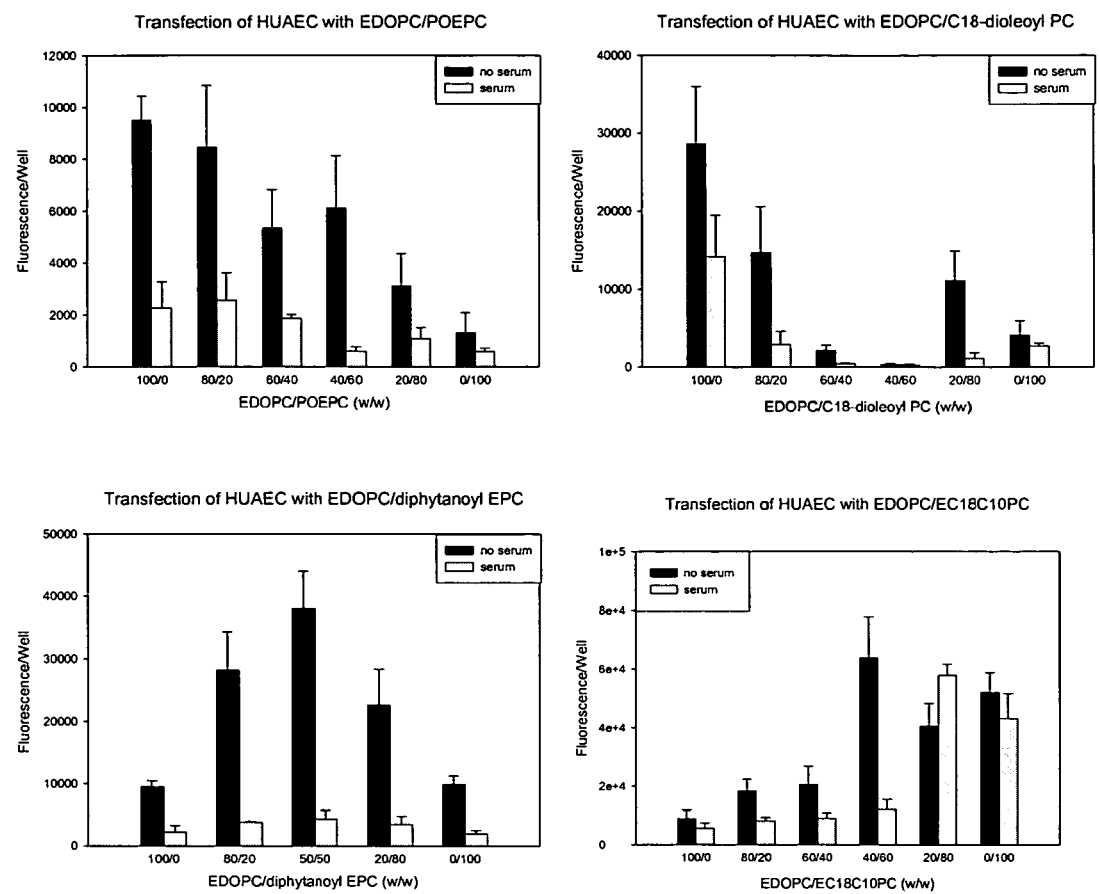
FIG. 10 shows the results of transfecting HUAECs with EDOPC/POEPC, EDOPC/EDiphytanoylPC, and EDOPC/SDOPC (DOPC with an 18 carbon chain instead of an ethyl group on the phosphate oxygen) mixtures.

Transfection of HUAECs with EDOPC/EPOPC, EDOPC/EDiphytanoylPC, EDOPC/SDOPC and EDOPC/EC18C10PC FIG. 10 shows the results of transfecting HUAECs with EDOPC/EPOPC, EDOPC/EDiphytanoylPC, EDOPC/ SDOPC (DOPC with an 18 carbon chain instead of an ethyl group on the phosphate oxygen), and EDOPC/EC18C10PC mixtures.

Example 4

Synthesis of New Cationic Phospholipoids (Derivatives of Phosphatidylcholine) Having Hydrophobic Moieties New cationic phospholipids (derivatives of phosphatidylcholine) are contemplated including, but not limited to, medium chain cationic PC's with phosphate oxygen alkyl substituents ranging in length from 2 to 24 C's); lyso cationic PC's with one long chain (C24) and a phosphate oxygen alkyl substituent with 2 to 12 C's; cationic PC's with acyl groups having very much different chain lengths; tetra-acyl cationic PC's with short acyl chains; and lipoids with very long (>18 carbons) acyl chains. In some cases, acyl or alky substituents may be branched so as to effectively increase the number of chains without increasing the number of attachment points to the hydrophilic cationic head group.

All publications and patents mentioned are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

TABLE 1

Cell viability and X-gal staining

| EDLPC/ EDOPC | Lipids/DNA | µg DNA/ well | Serum | Cell viability % | X-gal staining % |
|---|---|---|---|---|---|
| 80:20 | 4:1 | 0.5 | − | 77.5 | ~15 |
| 80:20 | 4:1 | 0.5 | + | 94.7 | n.d.* |
| 60:40 | 6:1 | 1.0 | − | 40.0 | n.d.* |
| 60:40 | 6:1 | 1.0 | + | 82.6 | 15 |

*Not determined

We claim:

1. A composition comprising: lipoid transfection reagents comprising a combination of cationic lipids selected from the group consisting of: EDLPC and EDOPC, EDLPC and EDMPC, EDOPC and di-C14-dimethlyammonium, EDOPC and EDiphytanoyl PC, and ditetradecyldimethylammonium and dioctadecylammonium, wherein said transfection reagents have a higher transfection efficiency compared to said reagents that have only one member of said combination of cationic lipids.

2. The composition of claim 1, further comprising a nucleic acid sequence.

3. The composition of claim 2, wherein said nucleic acid sequence comprises a transgene.

* * * * *

UNITED STATES PATENT AND TRADEMARK OFFICE
CERTIFICATE OF CORRECTION

PATENT NO. : 7,732,420 B2  Page 1 of 1
APPLICATION NO. : 10/957977
DATED : June 8, 2010
INVENTOR(S) : Robert C. MacDonald et al.

It is certified that error appears in the above-identified patent and that said Letters Patent is hereby corrected as shown below:

Column 1, lines 8-10 should read: --This invention was made with government support under Grant No. GM052329 awarded by the National Institutes of Health. The government has certain rights in the invention.--

Signed and Sealed this

Tenth Day of August, 2010

David J. Kappos
*Director of the United States Patent and Trademark Office*